US009006494B2

(12) United States Patent
Stecker et al.

(10) Patent No.: US 9,006,494 B2
(45) Date of Patent: Apr. 14, 2015

(54) PROCESS FOR PRODUCING VANILLIN FROM VANILLIN-COMPRISING COMPOSITIONS

(71) Applicants: BASF SE, Ludwigshafen (DE); Johannes-Gutenberg-Universität, Mainz (DE)

(72) Inventors: Florian Stecker, Mannheim (DE); Andreas Fischer, Hemsbach (DE); Axel Kirste, Limburgerhof (DE); Agnes Voitl, Schifferstadt (DE); Chung Huan Wong, Mannheim (DE); Siegfried Waldvogel, Mainz (DE); Carolin Regenbrecht, Mannheim (DE); Dominik Schmitt, Harxheim (DE); Marius Franziskus Hartmer, Mainz (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/934,806

(22) Filed: Jul. 3, 2013

(65) Prior Publication Data

US 2014/0046099 A1    Feb. 13, 2014

Related U.S. Application Data

(60) Provisional application No. 61/667,968, filed on Jul. 4, 2012.

(51) Int. Cl.
*C07C 45/79* (2006.01)

(52) U.S. Cl.
CPC .................................. *C07C 45/79* (2013.01)

(58) Field of Classification Search
USPC ................................................. 568/436, 438
See application file for complete search history.

(56) References Cited

U.S. PATENT DOCUMENTS

| | | | |
|---|---|---|---|
| 2,449,364 | A | 9/1948 | Blankart |
| 2011/0089046 | A1 | 4/2011 | Griesbach et al. |

FOREIGN PATENT DOCUMENTS

| | | |
|---|---|---|
| CH | 245 671 | 11/1946 |
| CH | 24561 | 7/1947 |
| WO | WO81/02113 | 8/1981 |
| WO | WO-8703014 A1 | 5/1987 |
| WO | WO-2009138368 A1 | 11/2009 |

OTHER PUBLICATIONS

"Isolating Vanillin", Database Accession No. 44:3207, dated Apr. 22, 2001.
Bjorsvik, H., "Fine Chemicals from Lignosulfonates. 1. Synthesis of Vanillin by Oxidation of Lignosulfonates", Organic Process Research & Development, vol. 3, (1999), pp. 330-340.
Brauns, F., et al., "The Chemistry of Lignin", Academic Press Inc., (1952), pp. 511-535.
Doree, C., "Transactions", Journal of The Chemical Society, (1913), pp. 677-686.
Leopold, B., et al., "Aromatic Keto- and Hydroxy-polyethers as Lignin Models. III", Acta Chemica Scandinavica, vol. 4, (1950), pp. 1523-1537.
Leopold, B., et al., "III. Oxidation of Wood from *Picea abies* (L.) Karst. (Norway Spruce) with Nitrobenzene and Alkali", Acta Chemica Scandinavica, vol. 6, (1952), pp. 38-48.
Pepper, J., et al., "Lignin oxidation. Preferential use of cupric oxide", Canadian Journal of Chemistry, vol. 45, (1967), pp. 3009-3012.
Pepper, J., et al., "The Isolation and Properties of Lignins Obtained by the Acidolysis of Spruce and Aspen Woods in Dioxane-Water Medium", Can. J. Chem., vol. 37, (1959), pp. 1241-1248.
Smith, C., et al., "Electro-organic reactions. Part 60[1]. The electro-oxidative conversion at laboratory scale of a lignosulfonate into vanillin in an FM01 filter press flow reactor: preparative and mechanistic aspects", J. Appl. Electrochem, vol. 41, (2011), pp. 363-375.
Zabkova, M., et al., "Recovery of vanillin from Kraft lignin oxidation by ion-exchange with neutralization", Separation and Purification Technology, vol. 55, (2007), pp. 56-68.
Zabkova, M., et al., "Recovery of vanillin from lignin/vanillin mixture by using tublar ceramic ultrafiltration membranes", Journal of Membrane Science, vol. 301, (2007), pp. 221-237.
Andreeva, L., et al., "Sorption isolation of vanillin using the MVP-3anion", Khimiko-Farmatsevticheskii Zhurnal, Database Caplus Accession No. 1972: 530543, dated 1972, pp. 44-47.
Andreeva, L., et al., "Thermodynamic Functions of the Sorption Process of Vanillin With Anion-Exchange Resin MVP-3", Pharmaceutical Chemistry Journal, vol. 8, No. 8, (1974), pp. 487-489.
Borges Da Silva, E., et al., "An integrated process to produce vanillin and lignin-based polyurethanes from Kraft lignin", Chemical Engineering Research and Design, vol. 87, (2009), pp. 1276-1292.
International Search Report for PCT/EP2013/064066, dated Sep. 16, 2013,.
Larikova, I., et al., "Purification of vanillin using a combined extraction/ion-exchange sorption process", Database Caplus Accession No. 1989: 120975, (1988), pp. 691-692.
Parpot, P., et al., "Biomass conversion: attempted electroxidation of lignin for vanillin production", Journal of Applied Electrochemistry, vol. 30, (2000), pp. 727-731.
Smith, C., et al., "Electro-organic reactions. Part 60[1]. The electro-oxidative conversion at laboratory scale of a lignosulfonate into vanillin in an FM01 filter press flow reactor: preparative and mechanistic aspects", J. Appl. Electrochem., vol. 41, (2011), pp. 363-375.

*Primary Examiner* — Sikarl Witherspoon
(74) *Attorney, Agent, or Firm* — Drinker Biddle & Reath LLP

(57) ABSTRACT

The present invention relates to a process for producing vanillin from an aqueous, basic vanillin-comprising composition, in particular from a composition as arises in the oxidation, especially in the oxidation by electrolysis, of aqueous alkaline lignin-comprising compositions, comprising at least one treatment of an aqueous, basic vanillin-comprising composition, in particular the treatment of a composition as arises in the oxidation, especially in the oxidation by electrolysis, of aqueous alkaline lignin-comprising compositions, with a basic adsorbent, in particular an anion exchanger.

18 Claims, No Drawings

PROCESS FOR PRODUCING VANILLIN FROM VANILLIN-COMPRISING COMPOSITIONS

CROSS-REFERENCE TO RELATED APPLICATIONS

This application claims benefit (under 35 USC 119(e)) of U.S. Provisional Application 61/667,968, filed Jul. 4, 2012, which is incorporated by reference.

The present invention relates to a process for producing vanillin from aqueous, basic vanillin-comprising compositions as arise, for example, in the oxidation of alkaline, aqueous lignin-comprising solutions or suspensions.

The transformation of renewable raw materials to valuable chemicals, which are suitable, particularly, as fragrances and aroma substances, is of very great interest. Lignin and also lignin-comprising substances such as alkali lignin, lignin sulfate or lignin sulfonate arise as waste materials or byproducts of wood processing to give pulp. The total production of lignin-comprising substances is estimated at about 20 billion tons per year. Lignin is thus a valuable raw material. Parts of this lignin are in the interim further used. For example, alkali lignin, which can be produced by alkaline treatment of the black liquor arising in paper manufacture, is used in North America as a binder for particle boards based on wood and cellulose, as dispersants, for clarifying sugar solutions, stabilizing asphalt emulsions and also foam stabilization. However, by far the greatest amount of waste lignin is used via combustion as an energy source, e.g. for the pulp process.

The biopolymer lignin is a group of three-dimensional macromolecules occurring in the cell wall of plants that are composed of various phenolic monomer building blocks such as p-coumaryl alcohol, coniferyl alcohol and sinapyl alcohol. On account of its composition, it is the sole significant source of aromatics in nature. The use of this renewable natural material, in addition, does not compete with a use as food.

Vanillin, 4-hydroxy-3-methoxybenzaldehyde, is a synthetic aroma substance which is widely used instead of expensive natural vanilla as an aroma substance for foods, as a fragrance in deodorants and perfumes, and also for flavor enhancement of pharmaceuticals and vitamin preparations. Vanillin is also an intermediate in the synthesis of various medicaments such as, e.g., L-dopa, methyldopa and papaverin.

To date, aromatic aldehydes have generally been produced from petrochemical precursors. On account of the structural similarity of vanillin to the building blocks of lignin, lignin should be suitable as a starting material for producing vanillin. The oxidative cleavage of lignin to vanillin and other aromatic aldehydes has therefore been the subject of numerous studies since the 1940s. The most frequently used conversions of lignin are chemical oxidation with copper oxide (see J. M. Pepper, B. W. Casselman, J. C. Karapally, Can. J. Chem. 1967, 45, 3009-3012) or nitrobenzene (see B. Leopold, Acta. Chem. Scand. 1950, 4, 1523-1537; B. Leopold, Acta. Chem. Scand. 1952, 6, 38-39), acidolysis (see J. M. Pepper, P. E. T. Baylis, E. Adler, Can. J. Chem. 1959, 37, 1241-1248), hydrogenolysis (see F. E. Brauns, Academic Press 1952, New York, 511-535) or ozonolysis (C. Doree, M. Cunningham, J. Chem. Soc. 1913, 103, 677-686). One of the leading methods is treating lignin with oxygen at temperatures above 100° C. in an alkaline medium in the presence of copper or cobalt catalysts (see H. R. Bjorsvik, Org. Proc. Res. Dev, 1999, 3, 330-340).

On occasions, the preparation of vanillin from lignin by electrolysis of aqueous alkaline lignin-comprising suspensions or solutions has been reported—see WO 87/03014, WO 2009/138368 and C. Z. Smith et al. J. Appl. Electrochem. 2011, DOI 10.1007/s10800-010-0245-0.

For the production of vanillin from the basic reaction solutions of such an oxidation, in addition to a conventional extraction, optionally after acidification, various processes are known.

The extraction of vanillin or vanillate from basic lignin solutions succeeds, for example, via cation exchange, with neutralization of the basic solution. In this case, the vanillate is passed through a cation-exchanger resin in the $H^+$ form, whereby it is protonated to form vanillin. This cation exchange is coupled to neutralization in the presence of a buffer solution (vanillate/vanillin)—see M. Zabková et al., Sep. Purif. Technol. 2007, 55, 56-68. It proved to be disadvantageous that the vanillin is not extracted from the solution. Therefore, this method does not offer any protection against overoxidation. In addition, large amounts of acid are required for neutralization of the basic reaction medium. By acidification, the lignin precipitates out of the solution, needs to be filtered off and thus can cause a loss of vanillin due to filtration.

CH 245671 describes the production of vanillin from aqueous solutions comprising impurities, the aqueous solution first adsorbing the vanillin on a basic ion exchanger which comprises amino groups, and then being eluted with an acid. In this regard, in the examples, the humic acid present is precipitated out of the aqueous solutions by acidification, and the pH of the aqueous solution of vanillin is then set to 7.

Precipitation out of the lignin can be bypassed by, e.g., extracting sodium vanillate directly from the alkaline solution using n-butyl alcohol or isopropanol. However, this extraction is limited by the poor solubility of the vanillate salts in organic solvents. In addition, this method has the disadvantage that the extracted fraction of unreacted lignin is very great and is therefore unavailable to the oxidation.

In addition, the removal of vanillin from the alkaline aqueous reaction streams arising in the oxidation of Kraft lignin using ultrafiltration through tubular ceramic membranes is known—see M. Zabková et al., J. Membr. Sci. 2007, 301(1-2), 221-237. Disadvantages are the comparatively high expenditure on an ultrafiltration and the costs associated therewith and the low capacity. Thus, efficient separation of the vanillin is only possible at low permeation rates. Membranes that permit higher permeation rates lead to increased discharge of the lignin, the separation of which requires further separation steps and in addition is removed from the oxidation. Furthermore, the oxidic membrane structures are unsuitable for long exposure in the alkaline medium, since they are subject to corrosion.

The object of the invention is to provide a robust process for producing vanillin from aqueous alkaline vanillin-comprising compositions, which process does not require neutralization of the composition. The process should be suitable, in particular, for producing vanillin from alkaline, aqueous compositions, as arise in the oxidation of aqueous alkaline lignin-comprising compositions which, in addition to vanillin, also comprise lignin and polymeric oxidation products. These solutions typically have pHs of at least 10, frequently at least 12 and in particular pHs above 13. In particular, the process should allow production of vanillin from these compositions without removing relatively large amounts of lignin together with the vanillin. The process should be suitable, in addition, for removing vanillin from the aqueous alkaline reaction mixtures arising in the oxidation during the oxidation process, in order in this manner to decrease the risk of overoxidation of the vanillin.

This and other objects are achieved by the process described hereinafter, in which an aqueous, basic vanillin-comprising composition, in particular a composition as arises in the oxidation, especially in the oxidation by electrolysis, of aqueous alkaline lignin-comprising compositions, is treated with a basic solid adsorbent, in particular an anion exchanger.

The present invention therefore relates to a process for producing vanillin from an aqueous, basic vanillin-comprising composition, in particular from a composition as arises in the oxidation, especially in the oxidation by electrolysis, of aqueous alkaline lignin-comprising compositions, comprising at least one treatment of an aqueous, basic vanillin-comprising composition, in particular the treatment of a composition as arises in the oxidation, especially in the oxidation by electrolysis, of aqueous alkaline lignin-comprising compositions, with a basic solid adsorbent, in particular an anion exchanger.

The process according to the invention is linked to a number of advantages: since the vanillin is present as a weak acid in the alkaline, aqueous composition, predominantly or completely in anionic form, i.e. as vanillate, it is adsorbed by the adsorbent and can then be liberated or eluted in a simple manner by treatment with a suitable eluent, typically with an acid, in particular with a dilute solution of a mineral acid in an organic solvent or in an aqueous-organic solvent mixture. Introduction of acid into the basic or alkaline composition can be avoided thereby. This allows, in the case of aqueous compositions that arise in the oxidation of alkaline, aqueous compositions of lignin-comprising compositions, a discharge of the vanillin formed in the oxidation during the oxidation, in such a manner that firstly the risk of overoxidation of the vanillin is decreased and secondly the vanillin-depleted aqueous lignin-comprising composition can be returned directly to the oxidation. In this manner, the conversion of the lignin can be maximized and the total yield of aromatic compounds increased. This allows a virtually complete utilization of the renewable raw material lignin. The vanillin liberated from the adsorbent is in addition highly prepurified and comprises very much smaller amounts of lignin than in the processes of the prior art. In addition, the salt load can be significantly decreased, since the entire basic reaction mixture need not be neutralized but only the vanillate bound to the adsorbent.

The process primarily has the advantage that it can be carried out directly with basic or alkaline solution of vanillin, which can still comprise large amounts of impurities, even at pHs of at least 10, in particular at least pH 12 or even at pHs above 13. It is surprising that vanillin be adsorbed from basic solution by the basic adsorbent even at these pHs, since, owing to the relatively low charge density of the vanillate anion and the comparatively high concentration of OH⁻ ions at these pHs, one would have expected that the OH⁻ ions displace the vanillate anion and no significant adsorption of the vanillate to the basic adsorbent takes place.

The process according to the invention allows in this manner a repeated or continuous oxidation of lignin in the alkaline medium with simultaneous, repeated or continuous production of vanillin. Production of vanillin using the solid basic adsorbent is particularly economical, since the basic adsorbent may be readily regenerated and used repeatedly to produce the vanillin.

Here and hereinafter, the expressions "basic vanillin solution", "alkaline vinillin solution", "basic composition", "alkaline composition", "basic aqueous vanillin-comprising composition", "alkaline aqueous vanillin-comprising composition", "basic vanillin solution", "alkaline vanillin solution" and "alkaline composition" are used synonymously.

These are taken to mean aqueous compositions which comprise vanillin in dissolved form, optionally in addition to impurities, and which have a basic or alkaline pH of generally above 9, frequently a pH of at least 10, in particular at least pH 12, and especially a pH above 13.

For the treatment of the basic or alkaline composition with the basic adsorbent, in particular the anion-exchanger resin, for example the adsorbent can be added to the alkaline aqueous vanillin-comprising composition. After a certain residence time, the basic adsorbent is separated off from the alkaline aqueous vanillin-comprising composition and then the vanillin is liberated from the absorbent by treatment with the eluent. The separation can proceed by usual processes of solid-liquid separation, e.g. by filtration, sedimentation or centrifugation.

Preferably, the composition is first passed through a bed, or fixed bed, of the basic adsorbent, for example a column packed with the adsorbent, and then the basic adsorbent is eluted with the eluent.

Suitable adsorbents are in principle all substances which comprise basic groups or are treated with hydroxide ions. These include alkalized activated carbons, basic aluminum oxides, clays, basic adsorber resins, in particular anion exchangers or anion-exchanger resins. Anion exchangers or anion-exchanger resins generally comprise functional groups which are selected from tertiary amino groups, quaternary ammonium groups and quaternary phosphonium groups.

The anion exchangers used are preferably crosslinked organic polymer resins which comprise cationic groups, for example quaternary ammonium groups, quaternary phosphonium groups, imidazolium groups or guanidinium groups, in particular quaternary ammonium groups or imidazolium groups.

In a preferred embodiment, the basic adsorbents used are anion-exchanger resins selected from the group of crosslinked polystyrene resins (hereinafter ion exchangers of the group i), where some of the phenyl rings of the crosslinked polystyrene bear quaternary ammonium groups, in particular those of the formula I:

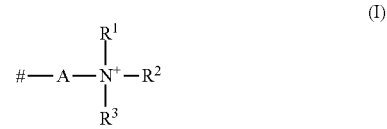

where $R^1$, $R^2$ and $R^3$, independently of one another, are $C_1$-$C_8$ alkyl, wherein one of the radicals $R^1$, $R^2$ or $R^3$ can also be $C_1$-$C_8$ hydroxyalkyl, A is $C_1$-$C_4$ alkanediyl, and # denotes the binding site to a phenyl group of the polystyrene resin.

Here and hereinafter, $C_1$-$C_8$ alkyl is a linear or branched aliphatic hydrocarbon radical having 1 to 8 carbon atoms, in particular having 1 to 4 carbon atoms ($C_1$-$C_4$ alkyl), such as, for example, methyl, ethyl, n-propyl, isopropyl, n-butyl, 2-butyl, n-pentyl, n-hexyl, n-heptyl or n-octyl.

Here and hereinafter, $C_1$-$C_8$ hydroxyalkyl is a linear or branched aliphatic hydrocarbon radical having 1 to 8 carbon atoms, in particular having 2 to 4 carbon atoms ($C_2$-$C_4$ hydroxyalkyl), that bears an OH group. Examples of such radicals are 2-hydroxyethyl, 3-hydroxypropyl, 2-hydroxypropyl, 4-hydroxybutyl and 6-hydroxyhexyl.

Here and hereinafter, $C_1$-$C_4$ alkanediyl is a bivalent aliphatic hydrocarbon radical having 1 to 4 carbon atoms, such as methylene ($CH_2$), ethane-1,1-diyl, ethane-1,2-diyl, propane-2,2-diyl, propane-1,2-diyl, propane-1,3-diyl, butane-1, 1-diyl, butane-2,2-diyl, butane-1,2-diyl, butane-1,3-diyl, butane-2,3-diyl or butane-1,4-diyl.

Among the adsorbents of the group i), chiefly, those are preferred where A, $R^1$, $R^2$ and $R^3$, independently of one another, and particularly preferably in combination, have the following meanings:

$R^1$, $R^2$, $R^3$, independently of one another, are methyl or ethyl and especially methyl;
A is methylene.

Adsorbents of the group i) are known and are commercially available, for example the Amberlite® types IRA400, IRA401, IRA402, IRA410, IRA458, IRA478, IRA900, IRA904, IRA910, FPA40, FPA 90, FPA 91 (Dow), Amberlyst® A26 (Dow), the Amberjet® types 4200, 4400 and 4600 (Dow), the Ambersep® types 900 and 920U (Dow), the Dowex® types Dowex Monosphere 550A OH, Dowex 1X100, 1X850 and 1X850 (Dow) and the Applexion® types XA4001, XA 4013, XA4023, XA4041, XA4042 and XA4043.

In a further preferred embodiment, the basic adsorbents used are anion-exchanger resins are crosslinked polyvinylpyridines (hereinafter ion exchangers of the group ii), in which some of the pyridine groups are present in quaternized form, for example as group of the formulae IIa or IIb, in particular IIa:

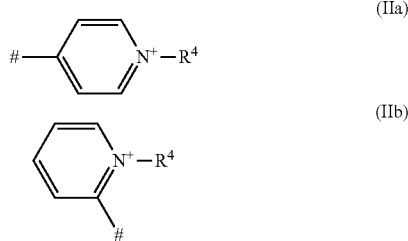

where $R^4$ is $C_1$-$C_8$ alkyl, in particular $C_1$-$C_4$ alkyl and especially methyl, and # denotes the binding site to a carbon atom of the polymer backbone of the polyvinylpyridine resin.

Adsorbents of the group ii) are known and are commercially available, for example the quaternized Reillex® HP types such as Reillex® HPQ.

In a further preferred embodiment, the basic adsorbents used are anion-exchanger resins are crosslinked acrylate resins (hereinafter ion exchangers of the group iii), in which some of the copolymerized monomers comprise quaternary ammonium groups, for example as group of the formula III:

where $R^5$, $R^6$ and $R^7$, independently of one another, are $C_1$-$C_8$ alkyl, A' is $C_2$-$C_4$ alkanediyl, and # denotes the binding site to an oxygen atom or nitrogen atom of a carboxyl group or carboxamide group bound to the polymer backbone of the acrylate resin.

Adsorbents of the group iii) are known and are commercially available, for example the Applexion® types XA 4122 and XA 4141 (Novasep).

Suitable adsorbents are also polymers which comprise N—$C_1$-$C_8$ alkylimidazolium groups (hereinafter ion exchangers of group iv). In these polymers, the N—$C_1$-$C_8$ alkylimidazolium groups are bound to the polymer backbone directly or via a spacer. Such polymers can be obtained by polymer-analogous reaction with N—$C_1$-$C_8$ alkylimidazole compounds, for example by reacting polymers comprising haloalkyl groups, in particular chlorobenzyl groups, e.g. copolymers of styrene and chloromethylstyrene, with N—$C_1$-$C_8$ alkylimidazoles. It is likewise possible to produce such polymers by homo- or copolymerization of monomers comprising imidazolium groups, for example (N—$C_1$-$C_8$ alkylimidazolium)methylstyrene, N-vinyl-N—$C_1$-$C_8$ alkylimidazolium, ω-(N—$C_1$-$C_8$-alkylimidazolium)-$C_2$-$C_8$-alkyl acrylate or ω-(N—$C_1$-$C_8$-alkylimidazolium)-$C_2$-$C_8$-alkyl methacrylate, optionally with comonomers such as $C_1$-$C_8$-alkyl acrylates, $C_1$-$C_8$-alkyl meth acrylates, $C_2$-$C_8$-hydroxyalkyl acrylates, $C_2$-$C_8$-hydroxyalkyl methacrylates or styrene, for example by free-radical polymerization or by controlled radical polymerization such as RAFT or ATRP. Such polymers are known and are described, for example, by J. Yuan, M. Antonietti, *Polymer* 2011, 52, 1469-1482; J. Huang, C. Tao, Q. An, W. Zhang, Y. Wu, X. Li, D. Shen, G. Li, *Chemical Communications* 2010, 46, 967; R: Marcilla, J. Alberto Blazquez, J. Rodriguez, J. A. Pomposo, D. Mecerreyes, *Journal of Polymer Science Part A: Polymer Chemistry* 2004, 42, 208-212; J. Tang, H. Tang, W. Sun, M. Radosz, Y. Shen, *Journal of Polymer Science Part A: Polymer Chemistry* 2005, 43, 5477-5489; J. Tang, Y. Shen, M. Radosz, W. Sun, *Industrial & Engineering Chemistry Research* 2009, 48, 9113-9118.

The anion-exchanger resins of groups i), ii), iii) and iv) can be macroporous or gel-type, wherein gel-type anion-exchanger resins, in particular gel-type anion-exchanger resins of group i), are preferably suitable.

Typically, the charge density, i.e. the number of ionic groups in anion-exchanger resins that are suitable according to the invention, is in the range from 0.5 to 5 mmol/g, in particular 1 to 4.5 mmol/g of ion exchanger resin (dry). Typically, the adsorbents or the anion-exchanger resins have a capacity for hydroxide ($OH^-$) ions in the range from 0.1 to 3 eq/l (mole equivalent per liter, moist), in particular in the range from 0.3 to 2.5 eq/l (moist) and especially in the range from 0.5 to 2 eq/l.

The basic adsorbents are particulate. The median particle size of the particulate adsorbents (weight-average diameter, determined, e.g. via sieve lines), is typically in the range from 10 μm to 2500 μm, and in particular in the range from 100 μm to 1000 μm, and especially in the range from 400 to 1000 μm. The adsorbents typically have particle sizes in the range from 10 to 650 mesh, in particular 15 to 350 mesh, and especially in the range from 15 to 60 mesh.

The polymer resins which are preferred according to the invention (anion exchangers or anion-exchanger resins) can be of gel type or macroporous. The particulate resins are typically in the form of macroscopic polymer particles, for example in the form of a powder or finely divided granules. The median particle size of the anion exchangers is typically in the range from 10 μm to 2000 μm, and in particular in the range from 100 μm to 1000 μm and especially in the range from 400 to 1000 μm (weight average, determined by sieving). They typically have particle sizes in the range from 10 to 650 mesh, in particular 15 to 350 mesh and especially in the range from 15 to 60 mesh.

In the process according to the invention, the adsorbent, in particular the anion-exchanger resin, can be used in its OH form, i.e. the groups present in the adsorbent, in particular in the anion-exchanger resin for charge neutralization are OH⁻ ions. The adsorbent, in particular the anion-exchanger resin, can also be used in the salt form, i.e. the cationic groups present in the anion-exchanger resin for charge neutralization are non-basic counterions such as chloride or sulfate. The OH form is then generated by the basic, aqueous vanillin composition and represents the actual adsorbent.

The vanillin adsorbed by the adsorbent during the treatment of the aqueous, basic vanillin-comprising composition is desorbed from the adsorbent by treatment of the adsorbent with at least one eluent and can be produced in purified form from the eluent in this manner. Suitable eluents are, especially, solutions of acids, in particular mineral acids in organic solvents, and also solutions of acids, in particular mineral acids in organic-aqueous solvent mixtures. Through the treatment of the adsorbent with the eluent, the vanillinate ions adsorbed by the adsorbent are neutralized to give vanillin, which is then desorbed from the adsorbent.

Suitable organic solvents are, especially, those which are unrestrictedly miscible with water at 22° C., or at least dissolve in an amount of at least 200 g/l in water at 22° C. These include, especially, dimethyl sulfoxide, acetone, $C_1$-$C_4$ alkanols such as methanol, ethanol, isopropanol, n-propanol, 1-butanol, 2-butanol and tert-butanol, alkanediols such as glycol, 1,4-butanediol, and also cyclic ethers such as dioxane, methyltetrahydrofuran or tetrahydrofuran, nitrogen heterocycles, such as pyridine or N-methylpyrrolidine and mixtures. Preference is given to $C_1$-$C_4$ alkanols, and especially methanol. The organic solvents can also be used in a mixture with water. The water fraction will preferably not exceed 70% by volume, in particular 50% by volume, and especially 30% by volume, based on the total volume of organic solvent and water. Where, as eluents, solutions of acids are used, in particular mineral acids in organic-aqueous solvent mixtures, solutions of mineral acids such as hydrochloric acid, phosphoric acid, and in particular sulfuric acid are especially suitable. Solutions of organic carboxylic and sulfonic acids, in particular those having 1 to 3 carbon atoms such as methanesulfonic acid, formic acid, acetic acid and propionic acid, are also particularly suitable. Preferably, the solution of the acid has a concentration of acid in the range from 0.01 to 10 mol kg⁻¹, in particular 0.1 to 5 mol kg⁻¹.

The aqueous, basic vanillin-comprising composition is generally treated with the adsorbent, in particular the anion-exchanger resin at temperatures below 150° C., frequently at a temperature below 100° C., preferably at a temperature in the range from 10 to 150° C., and in particular 10 to 100° C., and especially in the range from 10 to 70° C. or 15 to 50° C.

For treating the aqueous, basic vanillin-comprising composition with the adsorbent, i.e. for loading the adsorbent, in particular the anion-exchanger resin with the vanillin, preferably, the basic vanillin-comprising composition is passed in a usual manner through an adsorbent arrangement, i.e. through one or more fixed beds of the adsorbent, e.g. through one or more columns which are packed with the adsorbent (e.g. the anion exchanger). The passage through can proceed either in a descending or else ascending manner. The passage through proceeds preferably at a specific flow rate (specific load) in the range from 0.2 to 35, in particular 0.5 to 10, in particular 1 to 10 bed volumes per hour or a volumetric flow rate in the range from 0.1 to 50 m/h.

The relative amount of aqueous alkaline composition and adsorbent is usually selected in such a manner that at least 35%, and in particular at least 50%, of the vanillin present in the aqueous alkaline composition are adsorbed by the adsorbent. The amount of aqueous, alkaline composition is generally 1 to 1500 times, in particular 2 to 1000 times the amount of the bed volume. Depending on the degree of adsorption, the effluent arising at the exit of the adsorbent arrangement, e.g. the column packed with adsorbent, can still comprise vanillin, in such a manner that the effluent can optionally be passed to a further adsorbent arrangement, e.g. a column packed with adsorbent.

The loading process can be followed by a wash step. For this purpose, water is passed through the adsorbent arrangement. The amount of wash water is at this stage usually 0.1 to 10 times the bed volume, in particular 0.5 to 5 times the bed volume. The wash water is generally passed through at a specific flow rate (specific load) in the range from 0.2 to 35, in particular 0.5 to 10, in particular 1 to 10 bed volumes per hour or at a volumetric flow rate in the range from 0.1 to 50 m/h. The resultant wash water can comprise small amounts of the vanillin and can then be combined with the effluent arising during loading. In contrast to the processes of the prior art, such a wash step is not required, and so a preferred embodiment of the process according to the invention does not comprise a wash step, and the elution proceeds directly after the loading.

The loading step or the optionally carried out wash step is followed by the elution of the vanillin. For this purpose, the eluent is passed through the adsorbent arrangement. The vanillin is desorbed hereby and eluted and the adsorbent, for example the anion-exchanger resin is regenerated. The amount of eluent is generally 0.1 to 20 times, in particular 0.5 to 10 times, e.g. 1 to 8 times the amount of the bed volume. The eluent is generally passed through at a specific flow rate (specific loading) in the range from 0.5 to 20, in particular 1 to 10, in particular 2 to 8 bed volumes per hour. After the elution, any cationic groups in the adsorbent are present in the salt form, Optionally, therefore, before the next loading, a regeneration to the OH form can be carried out, e.g. by treatment with an aqueous solution of an alkali metal hydroxide, e.g. with aqueous NaOH.

With respect to the temperatures and flow rate, that stated for loading applies. The elution can be carried out either in an ascending or descending manner. The elution can be carried out in the same direction as the loading or in the opposite direction thereto.

The elution can be followed by a further wash step, in order to remove impurities optionally present. For this purpose, water is passed through the anion-exchanger arrangement. The amount of wash water is usually 0.1 to 10 times, in particular 0.5 to 5 times, e.g. 2 to 4 times the bed volume. The wash water is generally passed through at a specific flow rate (specific load) in the range from 0.5 to 20, in particular 1 to 10, in particular 2 to 8 bed volumes per hour. The effluent arising during the wash step is generally fed as wastewater to a usual wastewater treatment or other workup.

The adsorbent arrangement can be operated batchwise and then comprises one or more, e.g. 2, 3 or 4, series-connected, stationary fixed beds packed with adsorbent. It can also be operated continuously and then generally comprises 5 to 50, and in particular 15 to 40, adsorbent beds which can be, e.g., a component of a "True Moving Bed" arrangement (see K. Tekeuchi J. Chem, Eng. Jpn., 1978, 11 pp. 216-220), a "Continuous Circulating Annular" arrangement (see J. P. Martin, Discuss. Farraday Soc. 1949, p. 7) or a "Simulated Moving Bed" arrangement, as described, for example, in U.S. Pat. No. 2,985,589 and WO 01/72689 and also by G. J. Rossiter et al. Proceedings of AIChE Conference, Los Angeles, Calif., November 1991 or H. J. Van Walsem et al., J. Biochtechnol. 1997 59, p. 127.

The eluate arising during the elution is worked up in a usual manner for producing the vanillin. Generally, first the acid is removed, for example by an aqueous-extractive workup, or neutralized by adding base and the salts that are formed are separated off. Optionally, the eluate can be concentrated in advance, e.g. by removing the solvent in a usual evaporator arrangement. The resultant condensate can be reused, for example in a subsequent elution.

In this manner, a vanillin-comprising crude product is obtained which optionally comprises other low-molecular-weight components such as acetovanillone or vanillic acid and also optionally other components of the aqueous composition used, for example lignin.

In principle, in the process according to the invention, any aqueous vanillin-comprising compositions can be used that have a basic pH, wherein the pH is generally above 9, frequently at least 10, in particular at least 12, and especially at least or above 13.

The concentration of vanillin in the aqueous, vanillin-comprising composition is typically in the range from 1 to 5000 mg/kg, in particular 5 to 2000 mg/kg. In a special embodiment, the vanillin concentration is in the range from 5 to 500 mg/kg, and especially in the range from 10 to 250 mg/kg. In another embodiment, the concentration of vanillin is in the range from 10 to 5000 mg/kg, and in particular in the range from 20 to 2000 mg/kg.

The aqueous vanillin-comprising compositions are typically liquids having a water content of generally at least 30% by weight, frequently at least 50% by weight, in particular at least 60% by weight, based on the total weight of the composition. Where the aqueous vanillin-comprising compositions comprise solids, before the treatment with the adsorbent, a filtration can be carried out, but this is not absolutely necessary.

The process according to the invention has, in particular, advantages when the aqueous, basic vanillin-comprising composition is an aqueous, alkaline lignin-comprising composition which, in addition to vanillin, comprises lignin or lignin derivatives, for example lignin sulfate, lignin sulfonate, Kraft lignin, alkali lignin, soda lignin, or Organosolv lignin or a mixture thereof, as lignin component and which has an alkaline pH, generally a pH of at least 9, frequently at least 10, in particular at least 12, and especially at least or above 13. The aqueous, alkaline lignin-comprising composition generally comprises 0.5 to 30% by weight, preferably 1 to 15% by weight, in particular 1 to 10% by weight, of lignin, based on the total weight of the aqueous, lignin-comprising composition.

The process according to the invention is suitable, in particular, for producing vanillin from aqueous, basic vanillin-comprising compositions which were obtained by partial oxidation, especially by electrolysis, of an aqueous, alkaline lignin-comprising suspension or solution.

The aqueous, alkaline lignin-comprising suspension or solution used for the partial oxidation typically has a pH of at least 10, in particular of at least 12, and especially of at least or above 13. The aqueous, alkaline lignin-comprising suspension or solution used for the oxidation generally comprises 0.5 to 30% by weight, preferably 1 to 15% by weight, in particular 1 to 10% by weight, of lignin, based on the total weight of the aqueous, lignin-comprising composition.

The aqueous alkaline solution or suspension used for the partial oxidation can be an aqueous solution or suspension that arises as byproduct in an industrial process such as the production of paper stock, pulp or cellulose, e.g. black liquor, and also the lignin-comprising wastewater streams from the sulfite process, the sulfate process, the Organocell or Organosolv process, the ASAM process, the Kraft process or the natural pulping process. The aqueous alkaline solution or suspension for the oxidation can be an aqueous solution or suspension which is prepared by dissolving a lignin or lignin derivative in aqueous alkali, e.g. lignin sulfate, lignin sulfonate, Kraft lignin, alkali lignin, soda lignin or Organosolv lignin, or a lignin that arises in an industrial process such as the production of paper stock, pulp or cellulose, e.g. lignin from black liquor, the sulfite process, the sulfate process, the Organocell or Organosolv process, the ASAM process, the Kraft process, or the natural pulping process.

As bases for adjusting the pH of the aqueous, alkaline lignin-comprising suspension or solution, especially inorganic bases can be used, e.g. alkali metal hydroxides such as NaOH or KOH, ammonium salts such as ammonium hydroxide and alkali metal carbonates such as sodium carbonate, e.g. in the form of soda. Preference is given to alkali metal hydroxides, in particular NaOH and KOH. The concentration of inorganic bases in the aqueous, lignin-comprising suspension or solution should not exceed 5 mol/l, in particular 4 mol/l, and is typically in the range from 0.01 to 5 mol/l, in particular in the range from 0.1 to 4 mol/l.

The partial oxidation of the aqueous, alkaline lignin-comprising suspension or solution can be carried out in a manner known per se, e.g. according to the methods described in the prior art cited at the outset, especially by controlled oxidation with atmospheric oxygen at elevated temperature in the presence of suitable transition metal catalysts, e.g. copper or cobalt catalysts (see H. R. Bjorsvik, Org. Proc. Res. Dev. 1999, 3, 330-340) or especially by electrolysis of aqueous alkaline lignin-comprising suspensions or solutions, as described, for example, in WO 87/03014, WO 2009/138368 or C. Z. Smith et al., J. Appl. Electrochem. 2011, DOI 10.1007/s10800-010-0245-0 or hereinafter.

In the preparation of the aqueous, alkaline vanillin-comprising composition, an aqueous electrolyte that comprises lignin or a lignin-comprising substance and which is present in the form of an aqueous suspension or solution is subjected to an electrolysis under alkaline conditions. In this case, the oxidation of the lignin or lignin derivative present takes place at the anode. At the cathode, typically, reduction of the aqueous electrolyte proceeds, e.g. with formation of hydrogen.

The electrode materials used for the electrolysis can be selected among the electrode materials known for these purposes such as nickel, silver, $RuO_xTiO_x$ mixed oxides, platinized metals such as platinized titanium or platinized niobium, platinum, graphite or carbon, or else among what are termed base alloys, such as Ni-base alloys, Co-base alloys, Fe-base alloys, Cu-base alloys or Ag-base alloys. The use of base alloys has not been described for this purpose to date in the prior art and is subject matter of a parallel patent application. It has proved to be advantageous if the electrodes used in the electrolysis, at least the anodes, comprise an electrode material which is selected from Co-base alloys, Fe-base alloys, Cu-base alloys, Ag-base alloys and Ni-base alloys, and especially from Co- and Ni-base alloys.

A base alloy is taken to mean an alloy which comprises at least 50% by weight, in particular at least 55% by weight, especially at least 58% by weight, e.g. 50 to 99% by weight, preferably 50 to 95% by weight, in particular 55 to 95% by weight, particularly preferably 55 to 90% by weight, and especially 58 to 90% by weight of the respective base metal (in the case of a Co-base alloy Co, in the case of a Cu-base alloy Cu, in the case of an Ni-base alloy Ni, in the case of an Ag-base alloy Ag, and in the case of an Fe-base alloy Fe) and at least one further alloy component, wherein the total amount of all further alloy components that are different from the base metal is typically at least 1% by weight, in particular at least 5% by weight, and especially at least 10% by weight, and is e.g. in the range from 1 to 50% by weight, preferably in the range from 5 to 50% by weight, in particular in the range from 5 to 45% by weight, particularly preferably in the range from 10 to 45% by weight, and especially in the range from 10 to 42% by weight, wherein all figures in % by weight refer in each case to the total weight of the alloy. Typical further alloy components are, especially, Cu, Fe, Co, Ni, Mn, Cr, Mo, V, Nb, Ti, Ag, Pb and Zn, but also Si, C, P and S. Preference is accordingly given to base alloys which comprise at least one further of the abovementioned alloy components different from the base metal. Preference, in particular with regard to their stability with simultaneously good selectivity, is given to Ni-base alloys, Fe-base alloys and Co-base alloys, in particular Ni-base alloys and Co-base alloys. Preference, in particular with regard to their selectivity with simultaneously satisfactory stability, is given to Cu-base alloys and Ag-base alloys.

Typical nickel-base alloys comprise substantially, i.e. at least 95% by weight, and in particular at least 98% by weight, and especially at least 99% by weight a1) 50 to 95% by weight, in particular 55 to 95% by weight, particularly preferably 55 to 90% by weight, and especially 58 to 90% by weight Ni and b1) 5 to 50% by weight, in particular 5 to 45% by weight, particularly preferably 10 to 45% by weight, and especially 10 to 42% by weight, of at least one further alloy component, selected from Cu, Fe, Co, Mn, Cr, Mo, W, V, Nb, Ti, Si, Al, C and S.

Among the Ni-base alloys, preference is given in particular to those which comprise 5 to 35% by weight, in particular 10 to 30% by weight, Cu as further alloy component. These alloys are hereinafter designated group 1.1. In addition to Cu, the base alloys of group 1.1 can comprise one or more of the following alloy components in an amount of up to 45% by weight, in particular up to 40% by weight: Fe, Co, Mn, Cr, Mo, W, V, Nb, Ti, Si, Al, C and S. Examples of Ni-base alloys of group 1.1 are alloys of the EN abbreviations NiCu30Fe (Monel 400) and NiCu30Al and also the Ni—Cu alloy of the following composition: 63% by weight Ni, 30% by weight Cu, 2% by weight Fe, 1.5% by weight Mn, 0.5% by weight Ti (Monel 500K).

Among the Ni-base alloys, preference is also given, in particular, to those that comprise 5 to 40% by weight, in particular 15 to 30% by weight, Cr as further alloy component. These alloys are hereinafter designated group 1.2. In addition to Cr, the base alloys of group 1.2 can comprise one or more of the following alloy components in an amount of up to 40% by weight, in particular up to 35% by weight: Fe, Co, Mn, Cu, Mo, W, V, Nb, Ti, Si, Al, C and S. Among the Ni-base alloys of group 1.2, preference is given in particular to those that comprise Mo, Nb and/or Fe as further alloy component, in particular of an amount of in total 1 to 30% by weight. Examples of Ni-base alloys of group 1.2 are alloys of the EN abbreviations NiCr19NbMo (Inconel® alloy 718) and NiCr15Fe (Inconel® alloy 600), NiCr22Mo19Fe5 (Inconel® 625), NiMo17Cr16FeWMn (Hastelloy® C276), an Ni—Cr—Fe alloy having a nickel content of 72-76% by weight, a Cr content of 18 to 21% by weight, a C content of 0.08-0.13% by weight and an Fe content of 5% by weight, and an Ni—Cr—Co—Mo alloy having a nickel content of 48 to 60% by weight, a Cr content of 19% by weight, a Co content of 13.5% by weight and an Mo content of 4.3% by weight (Waspaloy®). Among the Ni-base alloys, preference is also given in particular to those that comprise 5 to 35% by weight, in particular 10 to 30% by weight, Mo as further alloy component. These alloys are hereinafter designated group 1.3. In addition to Mo, the base alloys of group 1.3 can comprise one or more of the following alloy components in an amount of up to 40% by weight, in particular up to 35% by weight: Fe, Co, Mn, Cu, Cr, W, V, Nb, Ti, Si, Al, C and S. Among the Ni-base alloys of group 1.3, preference is given in particular to those that comprise Cr, Nb and/or Fe as further alloy component, in particular of an amount of in total 1 to 30% by weight. Examples of Ni-base alloys of group 1.3 are alloys of the EN abbreviations NiMo28 (Hastelloy® B and Hastelloy® B-2) and NiMo29Cr (Hastelloy® B-3).

Typical cobalt-base alloys comprise substantially, i.e. at least 95% by weight, and in particular at least 98% by weight, and especially at least 99% by weight:

a1) 50 to 95% by weight, in particular 55 to 95% by weight, particularly preferably 55 to 90% by weight, and especially 58 to 90% by weight Co and b1) 5 to 50% by weight, in particular 5 to 45% by weight, particularly preferably 10 to 45% by weight, and especially 10 to 42% by weight, of at least one further alloy component, selected from Cu, Fe, Ni, Mn, Cr, Mo, W, V, Nb, Ti, Si, P and C.

Among the Co-base alloys, preference is given in particular to those that comprise 5 to 40% by weight, in particular 7 to 30% by weight, Cr as further alloy component. These alloys are hereinafter designated group 2.1. In addition to Cr, the base alloys of group 2.1 can comprise one or more of the following alloy components in an amount of up to 40% by weight, in particular up to 35% by weight: Fe, Ni, Mn, Cu, Mo, W, V, Nb, Ti, Si, C and P. Among the Co-base alloys of group 2.1, preference is given in particular to those that comprise Mo, W and/or Fe as further alloy component, in particular of an amount of in total 1 to 30% by weight. Examples of Co-base alloys of group 2.1 are alloys of the compositions:

i. 53% by weight Co, 31% by weight Cr, 14% by weight Fe, 1.2% by weight C (Stellite® 4), ii. 65% by weight Co, 28% by weight Cr, 4.5% by weight W, 1.2% by weight C, 1.1% by weight Si (Stellite® 6), iii. 66.5% by weight Co, 28% by weight Cr, 5% by weight Mo, 0.5% by weight C (Stellite® 21), iv. 58-62% by weight Co, 25-30% by weight Cr, 5-10% by weight Mo (Vitallium types, e.g. Haynes alloy 21);

v. 59% by weight Co, 8.5% by weight Cr, 29.5% by weight Mo, 2.1% by weight Si (T 400).

Typical iron-base alloys are high-alloy stainless steels. They generally comprise substantially, i.e. at least 95% by weight, and in particular at least 98% by weight, and especially at least 99% by weight:

a1) 50 to 95% by weight, in particular 55 to 95% by weight, particularly preferably 55 to 90% by weight, and especially 58 to 90% by weight Fe and b1) 5 to 50% by weight, in particular 5 to 45% by weight, particularly preferably 10 to 45% by weight, and especially 10 to 42% by weight, of at least one further alloy component, selected from Cu, Co, Ni, Mn, Cr, Mo, W, V, Nb, Ti, Si, P, S and C.

Among the Fe-base alloys, in particular preference is given to chromium-comprising stainless steels which, in addition to the base metal, comprise Cr as alloy component, wherein the chromium content generally is in the range from 5 to 30% by weight, in particular 10 to 25% by weight. These alloys are hereinafter designated group 3.1. In addition to Cr, the base alloys of group 3.1 can comprise one or more of the following alloy components in an amount of up to 40% by weight, in particular up to 35% by weight: Co, Ni, Mn, Cu, Mo, V, Nb, Ti, Si, C, S and P. Among the Fe-base alloys of group 3.1, preference is given in particular to those that comprise Ni, Mo, V, Ti, Si and/or Nb as further alloy component, in particular of an amount of in total 1 to 30% by weight. Examples of Fe-base alloys of group 3.1 are chromium steels, e.g. X12Cr13, X6Cr17 and X20Cr13, chromium-nickel steels, e.g. X2CrNi12, X5CrNi18-10, X8CrNiS18-9, X2CrNi19-11, X2CrNi18-9, X10CrNi18-8, X1CrNi19-9, X2CrNiMo17-12-2, X2CrNiMo19-12, X2CrNiMo18-14-3, X2CrNiMoN18-14-3, X13CrNiMoN22-5-3, X6CrNiTi18-10, X6CrNiMoTi17-12-2, GX5CrNiMoNb19-11-2 and X15CrNiSi25-21, chromium-molybdenum steels, e.g. X12CrMoS17 and 25CrMo4, and also chromium-vanadium steels.

Typical copper-base alloys generally comprise substantially, i.e. at least 95% by weight, and in particular at least 98% by weight, and especially at least 99% by weight
a1) 50 to 95% by weight, in particular 55 to 95% by weight, particularly preferably 55 to 90% by weight, and especially 58 to 90% by weight Cu and
b1) 5 to 50% by weight, in particular 5 to 45% by weight, particularly preferably 10 to 45% by weight, and especially 10 to 42% by weight, of at least one further alloy component, selected from Ag, Pb, Ni and Zn.

Examples of Cu-base alloys of group 3.1 are nickel silver (alloy of 62% by weight Cu, 18% by weight Ni and 20% by weight Zn) and cupronickel (alloy of 75% by weight Cu and 25% by weight Ni).

In principle, as anode, any electrode type known to those skilled in the art can be used. This can comprise completely the respective electrode material or be a supported electrode that has an electrically conducting support that is coated with the electrode material. The electrodes used as anode can be, for example, electrodes in the form of expanded metals, grids or metal plates.

As cathode, in principle, any electrode known to those skilled in the art and suitable for electrolysis of aqueous systems can be used. Since reduction processes take place at the cathode and the lignin is oxidized at the anode, when a heavy metal electrode is used such as, for example, a nickel cathode, the loading of the vanillin with this heavy metal is so low that the resultant vanillin can be used without problems in the food industry. Preferably, the electrode materials exhibit a low hydrogen overvoltage. Preference is given here to electrodes that have an electrode material selected among nickel, Ni-base alloys, Co-base alloys, Fe-base alloys, Cu-base alloys, silver, Ag-base alloys, i.e. silver-rich alloys having a silver content of at least 50% by weight, $RuO_xTiO_x$ mixed oxides, platinized titanium, platinum, graphite or carbon, In particular, the electrode material of the cathode is selected among Ni-base alloys, Co-base alloys, Fe-base alloys, Cu-base alloys, particularly preferably among Ni-base alloys, Co-base alloys and Fe-base alloys, and especially among the base alloys of groups 1.1, 1.2, 1.3, 2.1 and 3.1.

In principle, as cathode, any electrode type known to those skilled in the art can be used. These can comprise completely the respective electrode material or be a supported electrode that has a support which is coated with the electrode material. Preference is given to electrodes that comprise the respective electrode material, in particular one of the abovementioned base alloys, especially one of the base alloys of groups 1.1, 1.2, 1.3, 2.1 and 3.1. The electrodes used as cathode can be, for example, electrodes in the form of expanded metals, grids or metal plates.

The arrangement of anode and cathode is not restricted and comprises, for example, arrangements of planar gratings and/or plates which can also be arranged in the form of a plurality of stacks of alternating polarity and cylindrical arrangements of cylindrically formed grids, gratings or tubes which can also be arranged in the form of a plurality of cylinders alternating in polarity.

For achieving optimum space-time yields, various electrode geometries are known to those skilled in the art. Advantageous electrode geometries are a bipolar arrangement of a plurality of electrodes, an arrangement in which a rod-type anode is enclosed by a cylindrical cathode, or an arrangement in which both the cathode and the anode comprise a wire grid and these wire grids are placed one over the other and rolled up cylindrically.

The anode and cathode can be separated from one another by a separator. In principle, as separators, all separators usually used in electrolysis cells are suitable. The separator is typically a porous flat structure arranged between the electrodes, e.g. a grating, grid, woven fabric or nonwoven, made of an electrically non-conducting material which is inert under the electrolysis conditions, e.g. a plastic material, in particular a Teflon material, or a Teflon-coated plastic material.

For the electrolysis, any electrolysis cells known to those skilled in the art can be used, such as a divided or undivided continuous-flow cell, capillary gap cell or plate stack cell. Particular preference is given to the undivided continuous-flow cell, e.g. a continuous-flow cell with circulation, in which the electrolyte is continuously conducted past the electrodes in circulation. The process can be carried out with good success both discontinuously and continuously. The electrolysis can likewise be carried out on an industrial scale. Corresponding electrolysis cells are known to those skilled in the art. All embodiments of this invention relate not only to the laboratory scale but also to the industrial scale.

In a preferred embodiment, the contents of the electrolysis cell are mixed. For this mixture of the cell contents, any mechanical agitators known to those skilled in the art can be used. The use of other mixing methods such as the use of Ultraturrax, ultrasound or jet nozzles is likewise preferred.

By applying the electrolysis voltage to the anodes and the cathodes, electric current is conducted through the electrolytes. In order to avoid side reactions such as overoxidation and detonating gas formation, generally a current density of 1000 $mA/cm^2$, in particular 100 $mA/cm^2$, will not be exceeded. The current densities at which the process is carried out are generally 1 to 1000 $mA/cm^2$, preferably 1 to 100 $mA/cm^2$. Particularly preferably, the process according to the invention is carried out at current densities between 1 and 50 $mA/cm^2$.

The total electrolysis time clearly depends on the electrolysis cell, the electrodes used and the current density. An optimum time can be determined by those skilled in the art by routine experiments, e.g. by sampling during the electrolysis.

In order to avoid a deposit on the electrodes, the polarity can be changed in short time intervals. The change in polarity can proceed at an interval of 30 seconds to 10 minutes. Preference is given to an interval of 30 seconds to 2 minutes. For this purpose, it is expedient that anode and cathode comprise the same material.

The electrolysis is generally carried out at a temperature in a range from 0 to 160° C., preferably 50 to 150° C., wherein anodes made of the abovementioned base alloys permit the electrolysis to be carried out at relatively low temperatures, without a loss in selectivity occurring. The electrolysis then preferably proceeds at temperatures in the range from 10 to 100° C., in particular in the range from 50 to 95° C., and especially in the range from 70 to 90° C. The electrolysis is generally carried out at a pressure below 2000 kPa, preferably below 1000 kPa, in particular below 150 kPa, e.g. in the range from 50 to 1000 kPa, in particular 80 to 150 kPa, It is particularly preferable to carry out the process according to the invention at a pressure in the range of atmospheric pressure (101±20 kPa).

The particular advantages of the invention come in useful, in particular, when the basic vanillin-comprising composition is prepared by oxidation, in particular by electrolysis, of an aqueous, alkaline lignin-comprising suspension or solution, and the vanillin formed in the oxidation is removed or depleted during the oxidation from the resultant basic vanillin-comprising composition by treating the basic vanillin-comprising composition with the adsorbent. In this manner, overoxidation of the vanillin is decreased and the yield of vanillin, based on lignin used, can be significantly increased.

The removal or depletion of the vanillin from the aqueous-alkaline reaction mixture arising in the oxidation can proceed at intervals or continuously. In the removal or depletion of the vanillin at intervals, the oxidation of the aqueous, alkaline lignin-comprising suspension or solution is interrupted and the resultant aqueous-alkaline reaction mixture is treated in the above-described manner with the adsorbent, in particular the anion exchanger. In the continuous removal or depletion of the vanillin, generally a stream of the aqueous-alkaline reaction mixture that arises in the oxidation is discharged from the oxidation reactor, e.g. an electrolysis cell, the stream is treated with the adsorbent, in particular with anion exchanger, and the stream that is depleted in vanillin in this manner is returned to the oxidation reactor.

For the removal or depletion of the vanillin at intervals or continuously from the aqueous-alkaline reaction mixture arising in the oxidation, preferably the reaction mixture or the discharged stream of the reaction mixture is passed in the above-described manner through a bed of the adsorbent and then the adsorbent is treated with a dilute solution of a mineral acid in at least one organic solvent or an aqueous-organic solvent mixture, wherein the vanillin that is adsorbed by the adsorbent is eluted.

The examples hereinafter serve for more detailed illustration of the invention.

Analysis:

The reaction products were analyzed by gas chromatography. In this process the stationary phase used was an HP-5 column from Agilent, 30 m in length, 0.25 mm in diameter and 1 μm in layer thickness. This column was heated by a temperature program in the course of 10 min at a heating rate of 10° C./min from 50° C. to 290° C. This temperature was held for 15 min. As carrier gas, hydrogen was used having a flow velocity of 46.5 mL/min.

Anion exchangers used:

Amberlite® IRA402(OH) from Dow: OH form of a crosslinked styrene/divinylbenzene copolymer having trimethylammonium groups bound via $CH_2$ in the form of gel-type particles (20 to 25 mesh) having a moisture content of 50 to 60%. The anion exchanger has a capacity of 1.2 meq/ml, based on a bed of the anion exchanger swollen with water, or 4.1 meq/g, based on solid (approximately 1.3 meq/ml in the chloride form).

Reillex® HPQ from Vertellius Specialities (Sigma Aldrich): Cl form of a crosslinked poly-4-vinylpyridine that was quaternized with methyl chloride and in the form of gel-type particles (particle size 300-1000 μm) having a moisture content of 55%. The anion exchanger has a capacity of 4.1 meq/g, based on solid.

Dowex Monosphere 550A OH from Dow: OH form of a crosslinked styrene/divinylbenzene copolymer having trimethylammonium groups bound via $CH_2$ in the form of gel-type particles (median particle size 590 μm) having a moisture content of 55 to 65%. The anion exchanger has a capacity of 1.0 meq/ml, based on a bed of the anion exchanger swollen with water.

Ambersep 900 OH from Rohm & Haas (now Dow): OH form of a crosslinked styrene/divinylbenzene copolymer having trimethylammonium groups bound via $CH_2$ in the form of gel-type particles (20 to 25 mesh) having a moisture content of 65%. The anion exchanger has a capacity of 0.8 meq/ml, based on a bed of the anion exchanger swollen with water.

Amberlite® IRA910(Cl) from Dow: Cl form of a crosslinked styrene/divinylbenzene copolymer having dimethyl-2-hydroxyethylammonium groups bound via $CH_2$ in the form of macroporous particles (16 to 50 mesh) having a moisture content of 52%. The anion exchanger has a capacity of 1.0 meq/ml, based on a bed of the anion exchanger swollen with water, or 3.8 meq/g, based on solid.

1-Methylimidazolium-Modified Resin I 99.7 g of poly(styrene-co-chloromethylstyrene) (75-150 μm, loading (chloromethylstyrene): 0.94 mmol/g) were suspended in 1000 ml of toluene and admixed with 46.97 g of 1-methylimidazole. The reaction mixture was stirred for 17.5 h at 110° C. The resin was filtered off and successively washed with 300 ml of toluene, 250 ml of 0.1 M HCl, 600 ml of demineralized $H_2O$ and 300 ml of methanol. Subsequently, the resin was dried by freeze drying. Weight: 110.30 g.

Elemental analysis: C, 85.74; H, 8.33; N, 2.44

The dry resin was allowed to swell in 900 ml of methanol/$H_2O$ 2:1 for 1 day and then filtered.

5 ml of the 1-methylimidazolium resin thus produced were packed in a separating column (diameter: 0.5-1.0 cm) and first flushed with demineralized $H_2O$, then with aqueous 1 M NaOH solution, then with aqueous 0.1 M $AgNO_3$ solution until chloride ions were no longer detectable. Then, the column was flushed with demineralized $H_2O$ until the wash water had a pH=7. The activity was examined by means of acid-base titration. The column was then flushed with 100 ml of aqueous 2.5% strength by weight NaCl solution and then flushed with demineralized water. The flushing solution was collected in a 250 ml volumetric flask. The flushing solution was titrated in 50 ml aliquots. The result of the titrimetric analysis after a plurality of successive activation cycles is summarized in the following table.

Total exclusion capacity (TEC) after successive activation cycles

| Activation cycle | TEC [meq/ml] |
| --- | --- |
| 1 | 0.2 |
| 2 | 0.23 |
| 3 | 0.21 |

1-Propylimidazolium-Modified Resin II (Production)

49.35 g of poly(styrene-co-chloromethylstyrene) (75-150 μm, loading (chloromethylstyrene): 0.94 mmol/g) were suspended in 500 ml of toluene and admixed with 30.87 g of 1-propylimidazole. The reaction mixture was stirred for 23 h at 110° C. The resin was filtered off and washed in succession with 300 ml of toluene, 300 ml of 0.1 M HCl, 600 ml of demineralized $H_2O$ and 300 ml of methanol. Subsequently, the resin was dried by freeze drying. Weight: 57.49 g.

Elemental analysis: C, 84.98; H, 9.02; N, 2.38

The dry resin was allowed to swell in 450 ml of methanol/$H_2O$ 2:1 for 1 day and then filtered off.

1-Pentylimidazolium-Modified Resin III (Production)

49.70 g of poly(styrene-co-chloromethylstyrene) (75-150 μm, loading (chloromethylstyrene): 0.94 mmol/g) were suspended in 500 ml of toluene and admixed with 38.78 g of 1-pentylimidazole. The reaction mixture was stirred for 23 h at 110° C. The resin was filtered off and washed in succession with 300 ml of toluene, 300 ml of 0.1 M HCl, 600 ml of demineralized $H_2O$ and 900 ml of methanol. Subsequently, the resin was dried by freeze drying. Weight: 55.82 g.

Elemental analysis: C, 85.12; H, 9.69; N, 2.19

The dry resin was allowed to swell in 450 ml of methanol/$H_2O$ 2:1 for 1 day and then filtered off.

EXAMPLE 1

2.513 g of Kraft lignin were placed in a one-pot cell (V=600 mL) without a cooling jacket and dissolved with stirring in 300 g of 1 M NaOH. 11 nickel plates (each 5.0 cm×2.1 cm) were connected in a bipolar manner at a spacing of 0.3 cm in such a manner that the cell comprised ten half-chambers. The solution was electrolyzed for approximately 9.7 hours (Q=700 C; based on electrolyte: Q=7000 C). The cell voltage established was in the range from 3.0 to 3.2 V. After the amount of charge had flowed through, the cell contents were brought to room temperature and placed on a column bed of Amberlite® IRA402(OH) ($m_{Amberlite}$=10.072 g, $d_{column}$=2 cm, h=5 cm). The ion exchanger used had been swollen in water for several hours previously. After the reaction solution had completely passed through the column material (i) (droplet rate: 1 drop/sec), the filtrate (ii) was again electrolyzed under the abovementioned conditions. In total, the solution was electrolyzed and filtered five times.

For production of the vanillin adsorbed by the anion exchanger, the anion exchanger was washed in portions using a 2% strength by weight solution of HCl in methanol ($V_{tot}$=250 mL, droplet rate: 1 drop/sec). The resultant filtrate was admixed with 150 mL of $H_2O$ and extracted three times, each time with 100 mL of dichloromethane. The combined organic phases were washed with 80 mL of saturated common salt solution, dried over $Na_2SO_4$ and freed from the solvent under reduced pressure. A bronze foam remained which was purified by column chromatography (d=2 cm, h=20 cm of silica gel 60) (eluent: cyclohexane/ethyl acetate in the volumetric ratio 3:2). Based on Kraft lignin used, 2.59% by weight of vanillin were obtained which contained 8% by weight of acetovanillone (GC fraction).

For workup of the filtrate, it was acidified with concentrated hydrochloric acid with cooling and the acidified filtrate was filtered through a bed of kieselguhr, in order to remove lignin that had precipitated out. The kieselguhr bed was thoroughly rinsed with dichloromethane. The aqueous phase was extracted three times, each time with 100 mL of dichloromethane. The combined organic phases were washed with 100 mL of saturated common salt solution, dried over $Na_2SO_4$ and freed from the solvent under reduced pressure. A viscous solid remained ($m_{RP}$=17.2 mg, 0.68% by weight, based on Kraft lignin used). Gas-chromatographic analysis gave the following typical composition (GC fractions): 68.9% vanillin, 9.5% acetovanillone, 21.6% vanillic acid.

EXAMPLE 2

The electrolysis was carried out in a similar manner to example 1 with the following change: the reaction solution, after the amount of charge had flowed through and cooling to room temperature had been performed, was placed on a column bed of Amberlite® IRA402(OH) ($m_{Amberlite}$=50 g, $d_{column}$=2 cm, h=24.5 cm). After carrying out the electrolysis and filtration five times, the workup proceeds in a similar manner to example 1.

The column chromatographic purification of the organic crude product gave the following typical composition, based on Kraft lignin used (% by weight): 2.54% by weight vanillin, 2.45% by weight guaiacol.

EXAMPLE 3

2.011 g of Kraft lignin were placed in a one-pot cell (V=600 mL) without a cooling jacket and dissolved with stirring in 300 g of 3 M NaOH. 11 plates of Monel 400K (4.9 cm×2.1 cm) were connected in a bipolar manner at a spacing of 0.3 cm, in such a manner that the cell comprised ten half-chambers. The solution was electrolyzed for approximately 7.8 hours (Q=560 C; based on electrolyte: Q=5600 C). The cell voltage established was in the range from 3.0 to 3.1 V. After the amount of charge had flowed through, the cell contents were brought to room temperature and placed on a column bed of Amberlite IRA402(OH) ($m_{Amberlite}$=40 g, $d_{column}$=2 cm, h=20 cm). The ion exchanger used had been swollen for several hours in water in advance. After the reaction solution had completely passed through the column material (droplet rate: 1 drop/sec), the filtrate was electrolyzed again under the abovementioned conditions. In total, the solution was electrolyzed and filtered five times.

For production of the vanillin adsorbed by the anion exchanger, the anion exchanger was washed in portions using a 2% strength by weight solution of HCl in methanol ($V_{tot}$=350 mL, droplet rate: 1 drop/sec). The resultant filtrate was admixed with 100 mL of $H_2O$ and extracted three times, each time with 150 mL of dichloromethane. The combined organic phases were washed with approximately 100 mL of saturated common salt solution, dried over $Na_2SO_4$ and freed from the solvent under reduced pressure. A bronze-colored foam remained which was purified by column chromatography (d=2 cm, h=20 cm of silica gel 60) (eluent: cyclohexane/ethyl acetate in the volumetric ratio 3:2). Based on Kraft lignin used, 2.47% by weight of vanillin contaminated with 8% by weight of acetovanillone (GC fraction) were obtained.

For workup of the filtrate, it was acidified with concentrated hydrochloric acid with cooling and the acidified filtrate was filtered through a bed of kieselguhr, in order to remove lignin that had precipitated out. The kieselguhr bed was thoroughly rinsed with dichloromethane. The aqueous phase was extracted three times, each time with 150 mL of dichloromethane. The combined organic phases were washed with 100 mL of saturated common salt solution, dried over $Na_2SO_4$ and freed from the solvent under reduced pressure. A viscous solid remained ($m_{RP}$=11.9 mg, 0.59% by weight, based on Kraft lignin used). Gas-chromatographic analysis gave the following typical composition (GC fractions): 75.2% vanillin, 11.0% acetovanillone.

EXAMPLE 4

Each 50 mg of vanillin were dissolved in each case in 50 ml of 1 M aqueous sodium hydroxide solution in a screw-top jar and admixed with 1 g of ion-exchanger resin that had been swollen in distilled water overnight in advance for approximately 18 hours. The suspension was shaken for 45 minutes at approximately 300 rpm, then filtered through a frit and rinsed twice with 10 ml of water.

For recovery of the vanillin adsorbed by the anion exchanger, the anion exchanger was filtered off from the basic solution of the vanillin through a frit and transferred from the frit into a screw-top jar with 20 ml of an acid methanolic solution (90% methanol, 10% concentrated hydrochloric acid). The frit was then thoroughly rinsed with dichloromethane. The suspension was again shaken for 45 minutes at approximately 300 rpm, again filtered through a frit, and this was thoroughly rinsed with approximately 15 ml of dichloromethane. The filtrate was admixed with 2 µl of n-hexadecane and 30 ml of water, extracted 3 times, each time with 30 ml of dichloromethane, washed with 30 ml of saturated common salt solution and then dried over $Na_2SO_4$. The solvent was removed under reduced pressure and the remaining light-yellow solid was analyzed by gas chromatography.

For workup of the filtrate, 2 µl of n-hexadecane were added to the filtrate and the solution was acidified by adding concentrated hydrochloric acid with ice cooling. The aqueous phase was extracted 3 times, each time with 30 ml of dichloromethane. The combined organic phases were washed with saturated common salt solution and then dried over $Na_2SO_4$. The solvent was removed under reduced pressure and the remaining light-yellow solid was analyzed by gas chromatography.

The amount of vanillin recovered each time from the two fractions (at least 95% of the amount originally used, i.e. >47.3 mg) were determined from the gas chromatogram using the internal standard n-hexadecane.

The results of the ion-exchange experiments in basic vanillate solutions with use of various ion-exchanger resins are summarized in table 1.

| Ex. | Anion exchanger | Vanillin from filtrate [%][a] | Vanillin from ion exchanger [%][a] |
|---|---|---|---|
| 4a | Reillex ® HPQ [b] | 30.86 | 69.14 |
| 4b | Amberlite ® IRA 910 CI [b] | 40.36 | 59.64 |
| 4c | Dowex Monosphere ® 550A OH | 9.55 | 90.45 |
| 4d | Ambersep ® 900 OH | 32.90 | 67.10 |
| 4e | Amberlite ® IRA 402 OH | 13.40 | 86.60 |

[a] % by weight, based on the total amount of recovered vanillin
[b] The ion exchangers were converted into their OH form before use thereof by treatment with 1M NaOH

EXAMPLE 5

5 ml of 1-methylimidazolium resin, as described hereinbefore, were packed into a separating column (diameter: 0.5-1.0 cm) and first flushed with demineralized $H_2O$, then with aqueous 1 M NaOH solution by means of aqueous 0.1 M $AgNO_3$ solution, no chloride ions were detectable any more. The ion-exchanger resin was flushed with demineralized $H_2O$ until the wash water had a pH=7. Subsequently, a solution of 49.4 mg of vanillin in 25 ml of aqueous 1 M NaOH was passed through the ion-exchanger resin by $N_2$ overpressure or gravitation. Then, the resin was flushed with 25 ml of demineralized $H_2O$ until the wash water had a pH=7. Thereafter, the ion-exchange resin was washed in succession with methanolic 4% strength by weight HCl solution and methanol. The two methanolic fractions were combined, the solvent was removed and the residue was admixed with demineralized $H_2O$. The resultant mixture was extracted with ethyl acetate, the combined organic phase was dried and the solvent was removed. The residue was taken up in ethyl acetate and the vanillin content quantified by means of gas-chromatographic analysis. In this manner, 42.2 mg of the vanillin used (=86% of the vanillin used) were recovered. After reactivation of the resin used, reproducible TEC were established by titration.

EXAMPLE 6

49.2 mg of vanillin dissolved in 1 M of NaOH (50 ml) is admixed with 1.03 g of ion-exchanger resin (Dowex Monosphere 550a OH) and shaken for 1 h (frequency: 300 rpm). The ion-exchanger resin was filtered off and the residue was washed with 10 ml of demineralized $H_2O$. The washed ion-exchanger resin was then admixed with 20 ml of methanolic 5% by weight $H_2SO_4$ and an additional 10 ml of methanol and shaken for 1 h (frequency: 300 rpm). The ion-exchanger resin was filtered off and the solvent of the filtrate removed under reduced pressure. The resultant residue was admixed with $H_2O$, the aqueous phase was extracted with toluene and the combined organic phases were dried over $MgSO_4$.

After removal of the toluene, the residue was taken up in ethyl acetate and the vanillin content quantified by means of gas-chromatographic analysis. In this manner, 40.1 mg of vanillin (=82% of the vanillin used) were recovered.

EXAMPLE 7

The procedure was performed in a similar manner to example 6, wherein a solution of 48.0 mg of vanillin in 1 M NaOH (50 ml) was used and this was admixed with 1.01 g of ion-exchanger resin (Dowex Monosphere 550a OH) and the suspension was shaken for 1 h (frequency: 300 rpm). The ion-exchanger resin that was filtered, after washing with 10 ml of demineralized $H_2O$, was admixed with 20 ml of methanolic 10% strength by weight acetic acid solution and an additional 10 ml of methanol and shaken for 1 h (frequency: 300 rpm). After workup, 39.3 mg of vanillin (=82% of the vanillin used) was recovered

EXAMPLE 8

The procedure was performed in a similar manner to example 6, wherein a solution of 49.2 mg of vanillin in 1 M NaOH (50 ml) was used and this was admixed with 1.02 g of ion-exchanger resin (Dowex Monosphere 550a OH) and the suspension was shaken for 1 h (frequency: 300 rpm). The ion-exchanger resin that was filtered off was, after washing with 10 ml of demineralized $H_2O$, admixed with 20 ml of a 10% strength by weight solution of acetic acid in ethyl acetate and an additional 10 ml of ethyl acetate and shaken for 1 h (frequency: 300 rpm). After filtration of the ion-exchanger resin and removal of the solvent at reduced pressure, the resultant residue was taken up in ethyl acetate and the vanillin content was quantified by means of gas-chromatographic analysis. In this manner, 42.2 mg of vanillin (=86% of the vanillin used) was recovered.

The invention claimed is:

1. A process for producing vanillin from an aqueous, basic vanillin-comprising composition, comprising at least one treatment of an aqueous, basic vanillin-comprising composition with a basic solid adsorbent wherein the aqueous, basic vanillin-comprising composition has a pH of at least 10.

2. The process according to claim 1, wherein the aqueous, basic vanillin-comprising composition is first passed through a bed of the basic adsorbent and then the basic adsorbent is eluted using a dilute solution of an acid in at least one organic solvent or in an aqueous-organic solvent mixture.

3. The process according to claim 2, wherein the dilute acid solution is selected from alcoholic solutions and aqueous/alcoholic solutions of a mineral acid.

4. The process according to claim 2, wherein the dilute acid solution is sulfuric acid.

5. The process according to claim 1, wherein the basic adsorbent is a crosslinked organic polymer resin which comprises functional groups selected from tertiary amino groups, quaternary ammonium groups and quaternary phosphonium groups.

6. The process according to claim 1, wherein the basic adsorbent is a crosslinked organic polymer resin which comprises quaternary ammonium groups or quaternary phosphonium groups.

7. The process according to claim 5, wherein the polymer resin comprises 0.1 to 3 molar equivalents per liter (wet) of functional groups.

8. The process according to claim 5, wherein the basic adsorbent is selected from
(i) crosslinked polystyrene resins that comprise functional groups of the formula I:

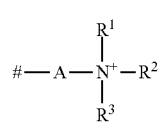

where $R^1$, $R^2$ and $R^3$, independently of one another, are $C_1$-$C_8$ alkyl, wherein one of the radicals $R^1$, $R^2$ or $R^3$ can also be $C_1$-$C_8$ hydroxyalkyl, A is $C_1$-$C_4$ alkanediyl, and # denotes the binding site to a phenyl group of the polystyrene resin;
(ii) crosslinked polyvinylpyridine resins that comprise functional groups of the formulae IIa and/or IIb:

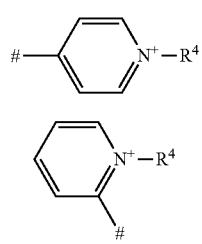

where $R^4$ is $C_1$-$C_8$ alkyl, and # denotes the binding site to a carbon atom of the polymer backbone of the polyvinylpyridine resin;
(iii) crosslinked acrylate resins that comprise functional groups of the formula III:

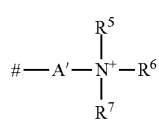

where $R^5$, $R^6$ and $R^7$, independently of one another, are $C_1$-$C_8$ alkyl, A' is $C_2$-$C_4$ alkanediyl, and # denotes the binding site to an oxygen atom or nitrogen atom of a carboxyl group or carboxamide group bound to the polymer backbone of the acrylate resin.

9. The process according to claim 1, wherein the basic adsorbent is selected from polymers which comprise N—$C_1$-$C_8$-alkylimidazolium groups.

10. The process according to claim 1, wherein the aqueous, basic vanillin-comprising composition has a pH of at least 13.

11. The process according to claim 1, wherein the aqueous, basic vanillin-comprising composition was obtained by oxidation of an aqueous, alkaline lignin-comprising suspension or solution.

12. The process according to claim 11, wherein the aqueous, basic vanillin-comprising composition was obtained by electrolysis of an aqueous, alkaline lignin-comprising suspension or solution.

13. The process according to claim 11, wherein the aqueous, alkaline lignin-comprising suspension or solution has a pH of at least 13.

14. The process according to claim 11, wherein, as aqueous, lignin-comprising suspension or solution, an aqueous lignin-comprising stream from the production of paper stock, pulp or cellulose is used.

15. The process according to claim 11, wherein the aqueous, alkaline lignin-comprising suspension or solution is prepared by dissolving or suspending at least one lignin-comprising material in aqueous alkali, wherein the lignin-comprising material is selected from lignin from black liquor, Kraft lignin, lignin sulfonate, alkali lignin, Organosolv lignin and corresponding residues from the paper industry, pulp or cellulose production.

16. The process according to claim 11, wherein the basic vanillin-comprising composition is prepared by oxidation.

17. The process according to claim 11, wherein the basic vanillin-comprising composition is prepared by by electrolysis, of an aqueous, alkaline lignin-comprising suspension or solution, and the vanillin formed in the oxidation is removed during the oxidation from the resultant basic vanillin-comprising composition by treating the basic vanillin-comprising composition with the basic adsorbent.

18. The process according to claim 16, wherein the basic vanillin-comprising composition arising during the oxidation is passed through a bed of the basic adsorbent and then the basic adsorbent is eluted with a dilute solution of an acid in at least one organic solvent or in an aqueous-organic solvent mixture.

* * * * *